United States Patent [19]

Spinelli et al.

[11] Patent Number: 5,104,895

[45] Date of Patent: Apr. 14, 1992

[54] PLATINUM(II) COMPLEXES, THEIR PREPARATION AND USE AS ANTI-TUMOR AGENTS

[75] Inventors: Silvano Spinelli; Alessandro Pasini; Ernesto Menta; Franco Zunino; Sergio Tognella, all of Milan, Italy

[73] Assignee: Boehringer Mannheim Italia S.p.A., Milan, Italy

[21] Appl. No.: 585,118

[22] PCT Filed: Mar. 25, 1989

[86] PCT No.: PCT/EP89/00330

§ 371 Date: Nov. 5, 1990

§ 102(e) Date: Nov. 5, 1990

[87] PCT Pub. No.: WO89/09218

PCT Pub. Date: Oct. 5, 1989

[30] Foreign Application Priority Data

Apr. 1, 1988 [IT] Italy .................. 20074 A/88

[51] Int. Cl.[5] .................. A61K 31/28; C07F 15/00
[52] U.S. Cl. .................. 514/492; 556/40; 556/137
[58] Field of Search .................. 549/206, 208, 212; 556/137, 40; 514/492

[56] References Cited

U.S. PATENT DOCUMENTS

| | | | |
|---|---|---|---|
| 4,565,884 | 1/1986 | Andrulis, Jr. et al. | 556/137 |
| 4,614,811 | 9/1986 | Grandolfi | 556/137 |
| 4,665,210 | 5/1987 | Bitha et al. | 556/137 |
| 4,687,780 | 8/1987 | Barnard | 556/137 |
| 4,730,069 | 3/1988 | Kolar et al. | 556/137 |
| 4,748,254 | 5/1988 | Cheltsov et al. | 556/137 |
| 4,760,155 | 7/1988 | Heffernan et al. | 556/137 |
| 4,845,124 | 7/1989 | Kidani et al. | 556/137 |
| 4,861,905 | 8/1989 | Nawatari et al. | 556/137 |
| 4,882,447 | 11/1989 | Tsujihara et al. | 556/137 |
| 4,886,894 | 12/1989 | Tsujihara et al. | 556/137 |
| 4,921,984 | 5/1990 | Nowatari et al. | 556/137 |
| 4,968,825 | 11/1990 | Yokoi et al. | 556/137 |
| 4,968,826 | 11/1990 | Totani et al. | 556/137 |
| 4,994,591 | 2/1991 | Anderson et al. | 556/137 |
| 5,008,419 | 4/1991 | Yokoi et al. | 556/137 |

FOREIGN PATENT DOCUMENTS 169645 1/1986 European Pat. Off. ............ 556/137

*Primary Examiner*—Cecilia Shen
*Attorney, Agent, or Firm*—Nikaido, Marmelstein, Murray & Oram

[57] ABSTRACT

Compounds of formula I $$T_1(-OCH_2CH_2)_{n1}-\underset{T_2(-OCH_2CH_2)_{n2}}{\overset{}{\diagdown}}(A)\underset{CO_2}{\overset{CO_2}{\diagup\diagdown}}(Pt)\underset{NH_2R_2}{\overset{NH_2R_1}{\diagup\diagdown}} \quad (I)$$

wherein $R_1$ and $R_2$, that can be the same or different, are hydrogen, alkyl, aryl, aralkyl groups or, if taken together, cycloalkyl groups;

A is a carbon atom, a residue of 2,3-dioxybutandioic-2,4-dioxyphtalic acid or disubstituted malonic acid derivatives;

$n_1$ and $n_2$ are selected in such a manner that the result of their addition is from 2 to 40;

$T_1$ and $T_2$ that can be the same or different, are hydrogen, alkyl, benzyl, phenyl, acyl or cycloalkyl or a residue of formulae $$\begin{array}{c}-CH-CO_2\\|\\-CH-CO_2\end{array}\underset{}{\overset{}{\diagup\diagdown}}Pt\underset{NH_2R_2}{\overset{NH_2R_1}{\diagdown}}$$

$$\begin{array}{c}-(CH_2)_2\\\\-(CH_2)_2\end{array}\underset{CO_2}{\overset{CO_2}{\diagup\diagdown}}C\underset{CO_2}{\overset{}{\diagup\diagdown}}Pt\underset{NH_2R_2}{\overset{NH_2R_1}{\diagdown}}$$

$$\underset{}{\diagdown}(CH_2)_m-C\underset{CO_2}{\overset{CO_2}{\diagup\diagdown}}Pt\underset{NH_2R_2}{\overset{NH_2R_1}{\diagdown}}$$

$$\underset{(CH_2)_m}{\overset{(CH_2)_m}{\diagup\diagdown}}C\underset{CO_2}{\overset{CO_2}{\diagup\diagdown}}Pt\underset{NH_2R_2}{\overset{NH_2R_1}{\diagdown}}$$

$$\underset{}{\diagdown}(CH_2)_m-C\underset{CO_2}{\overset{CO_2}{\diagup\diagdown}}Pt\underset{NH_2R_2}{\overset{NH_2R_1}{\diagdown}}$$

Compounds I are useful as anti-tumor agents in human therapy.

4 Claims, No Drawings

PLATINUM(II) COMPLEXES, THEIR PREPARATION AND USE AS ANTI-TUMOR AGENTS

The present invention relates to platinum(II) complexes useful as anti-tumour agents, to a method for their preparation and to pharmaceutical compositions containing them.

BACKGROUND OF THE INVENTION

It is well known the wide interest on platinum(II) and Platinum(IV) complexes as anti-tumour agents.

The anti-tumour activity of four platinum compounds in animal models was first reported in 1969 (B. Rosemberg et al., Nature 222, 385, 1969). This followed the observation that filamentous growth occurred when cultures of E. Coli were subjected to an electric field and the realization that certain cis-diamino-platinum complexes were the cause of this effect (B. Rosenberg et al., Nature, 205, 965, 1965).

The anti-tumour activity of said platinum(II) complexes has been demonstrated in several animal models. These compounds inhibit tumors such as ascitic leukaemia, Walker-256 carcinosarcoma, mammary tumors induced by dimethylbenzanthracene and B-16 ascitic melanoma. It is estimated that over 2,000 analogues of the original platinum compounds have been synthetized and tested throughout the world since that time.

For a review see P.C. Hydes and M.J.H. Russell, Cancer and metastasis reviews, 7, 67, 1988. Among these compounds, cis-diammino-dichloro-platinum (cDDP, cisplatin) has been the most studied one, and nowadays it has entered clinical practice after approval for the treatment of testicular and ovarian cancer in 1978.

Also other platinum(II) complexes have been studied successfully on animal models (see for example "Platinum, Gold and other metal chemotherapeutic agents", S. J. Lippard Ed., ACS Symp. Series, 209, Washington D.C., 1983).

The antitumour activity of cisplatin has been well-documented in patients affected with various tumours, being particularly effective in the treatment of genitourinary tumours, of neck and head tumours. Further clinical observations confirm efficacy of cisplatin in several human tumors, when administered in combination with other chemotherapeutic agents.

Due to important gastrointestinal and renal side-effects, haematologic and neurologic complications (ototoxicity) following cisplatin use, there is a increasing demand for novel platinum compounds provided with a better therapeutical index, and devoid of cross resistance with cisplatin.

Subsequent selection and evaluation processes resulted in the approval of carboplatin for use in the treatment of ovarian and small cell lung cancer in 1986. Carboplatin is reported to be less nephrotoxic than cis-platin.

Cisplatin and carboplatin (albeit at higher dose levels) show a similar spectrum of activity as other platinum compounds under clinical investigation.

At present time, the major requirement for a new drug is that it exerts a wider spectrum of clinical activity. In spite of all these efforts the results are not always encouraging both due to considerable toxicity and unfavourable lypophilic and hydrophilic properties of many of new platinum(II) complexes (see for example J. Clin. Hematol. Oncol. 12, 29, 1982). Poor solubility and stability in aqueous vehicles used for administration to patients represent one of the most serious obstacles for the clinical use of new compounds.

To overcome these difficulties, platinum(II) complexes endowed with additional basic or acid groups in neutral ligands and/or in leaving groups have been synthetized and screened The additional (basic and acid) functional groups were thought to be particularly suitable for achieving solubilization after salification of the complexes with an appropriate counter-ion at the moment of dissolution in aqueous media.

Examples of said compounds are for ex.: cis-diamino-2-amino-malonate-platinum(II) complexes (Gandolfi O., U.S. Pat. No. 4,614,811, 1986); bis-platinum(II) complexes disclosed in U.S. Pat. No. 4,565,884 wherein the central polyfunctionalized leaving group is provided with an additional acid group; aromatic dicarboxylato derivatives of diamino-cyclopentane platinum(II) containing $SO_3H$ and $CO_2H$ groups in the aromatic ring (D.C. Craciunescu et al., J. Pharm. Belg., 41, 286, 1986); water-soluble bis(ascorbato) platinum(II) complexes A. R. Amudsen and E. W. Stern, U.S. Pat. Nos. 4,457,926; 4,462,998; 4,505,928; M. P. Hacher et al., Cancer Res., 45, 4748, 1985). All these substances have been claimed to be effective anti-tumour agents.

Many of them, when tested in different animal models, were found to show higher activities than cisplatin in P368, L1210 and ADJ/PC6 murine tumour models, albeit sometimes at higher dose levels.

It should be noted that the drugs were administered i.p., the site of tumour implant, for both the P388 and L1210 tumour lines. It is also possible that a local, rather than systemic, antitumour effect was observed in many of these cases.

There is a very marked trend to believe that the presence of ionic charges in platinum(II) complexes would be strongly detrimental and limiting the permeability across cell membranes, thus hindering the diffusion inside the cells and consequently the systemic effectiveness.

The synthesis of platinum complexes with functionalised amine ligands was largely part of an attempt to vary the solubility characteristics of the complex and, indirectly, its tissue distribution. This was achieved in part by using a range of single functional groups e.g. hydroxyl and carboxylate substituents) that are expected to change the solubility of the parent compound. Amino and polyamino-sugars have been used as neutral ligands, too.

In order to improve activity, particularly on tumours that are refractory to platinum, toxicity or high dose levels are a necessary compromise unless a degree of selectivity can be conferred on the molecule.

One approach recently considered is to target the molecules to hormone receptor sites in a hormone dependent mammary carcinoma (see for ex. B. Wappes et al., J. Med. Chem., 27,1280, 1984).

An alternative approach for targeting platinum compounds uses immunoglobulins (Ig) with specific binding activity for particular cell types; or complexes attached to monoclonal antibodies against three Lewis Lung tumour lines (R. Arnon et al., Eur Pat. 0099133A 1984). Preliminary "in vivo" data suggest greater potency and lower toxicity than cisplatin and its analogues, although supportive data were not presented More recently, EP 0169645 has disclosed platinum(II) ccmplexes with very high selectivity of action when a malonate platinum(II)

complex is linked to a monoclonal antibody, preferably through a polymethylene chain that is connecting the leaving malonic residue of the platinum complex with the targeting antibody.

In the above-mentioned targeting monoclonal antibody platinum complexes, the connecting polymethylene may be also interrupted by oxygen atoms to form a polyoxyethylene chain. To this purpose, it is generically described the synthesis of intermediate malonate platinum(II) complexes wherein the $C_2$ carbon atom of the malonic leaving ligand is substituted by a —$(CH_2CH_2$—$O)_3H$ chain, and the final hydroxy group is suitably utilized for the desired conjugation with the monoclonal antibody. It is also generically disclosed that the single intermediate malonate platinum(II) complexes provided with polymethylene and/or polyoxyethylene chains, not bound with monoclonal antibody, may be effective as anti-tumour agents, although supportive data were not referred.

If one recalls that the preclinical evaluation of antitumour agents has relied upon animal tumours models, which are often poorly predictive of human cancer, then the difficulty of developing a drug with a new spectrum of activity becomes clear.

The design of cisplatin analogues for clinical application requires a judicious balance of the reactivity of the complex with its solubility in aqueous and lipid phases. While good water solubility is desiderable, it is generally achieved by using reactive leaving groups such as sulphate or nitrate, resulting in consequent toxicity, or chelating carboxylates that stabilise the molecule with a corresponding decrease in potency. In opposition, many compounds that show good anti-tumour activity in animal models are lipophilic and are administered as solutions or suspensions in peanut oil or as suspensions in aqueous media. The aqueous solubility of these compounds is too low to allow clinical evaluation of their properties via i.v. delivery.

The present invention relates to novel platinum(II) complexes which are endowed with intrinsically high solubility in aqueous media together with high lipophilic properties. The outstanding characteristics of the platinum(II) complexes of the present invention are achieved by the design of novel leaving ligands carrying polyoxyethylene substructures of increasing molecular weights. These substructures may be formed by linear polyoxyethylene chains and/or by cyclic polyoxyethylene residues, differently linked to malonic and to 1,4-butanedioic acids to better modulate the lipophilicity of the overall complex.

In accordance with the scope of the present invention the presence in the leaving group of linear and/or cyclic polyoxyethylene subunits of appropriate molecular weights enables to reach high solubilities in the aqueous media, and above all gives to the new molecules suitable lipophilic characteristics for improving their targeting to, penetration into and diffusion across the cell membranes.

In fact platinum(II) complexes of the present invention are provided both with hydrosolubility and with lipophilic properties. High hydrosolubility enables preparation of pharmaceutical compositions with high concentrations of the active principle; the administration of the drug to the patients may usefully result more comfortable, too. The more equilibrated balance of lipophilicity with hydrosolubility should favour high distribution of novel drugs in biological fluids, a proper interaction with cell membranes, an increased and selective tropism towards tumor cells, a wider spectrum of action, long-lasting biological effects and consequently more favourable therapeutical index.

DESCRIPTION OF THE INVENTION

More particularly, the present invention relates to platinum(II) complexes of formula (I):

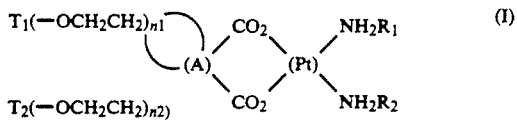

wherein $R_1$ and $R_2$, that can be the same or different, are hydrogen, linear or branched $C_1$-$C_6$-alkyl, $C_3$-$C_6$-cycloalkyl, phenyl, benzyl or, taken together, they represent one of groups of formula

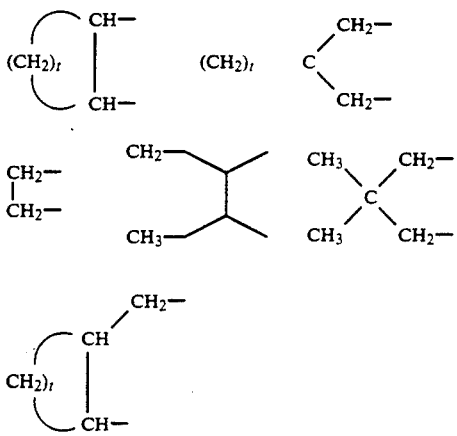

wherein t is an integer from 2 to 5;

(A) is a tetrasubstituted carbon atom or, taken together with the adjacent carboxylate groups, is a residue of a dietherified 2,3-dihydroxy-1,4-butanedioic acid, or a residue of mono or disubstituted malonic acids of the the following formulae:

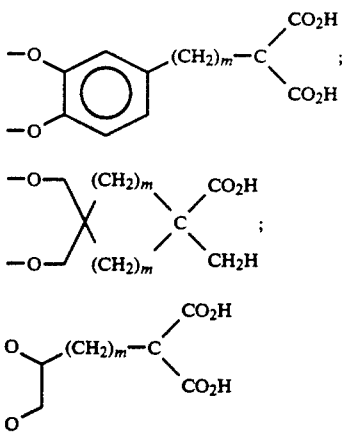

m is the integer 1 or 2;

each of $n_1$ and $n_2$, that may be the same or different, may be independently zero or an integer from 1 to 20 with the proviso that always the overall value of n ($n_1+n_2$) is a number comprised between 2 and 40 so that the overall number of the ethyleneoxy units —(C-

H$_2$—CH$_2$—O)$_n$—gives a ponderal contribution to the molecular weight of the complex ranging from 88 to 9000 Dalton;

T$_1$ and T$_2$, that can be the same or different, are selected from the group consisting of hydrogen, linear or branched C$_1$C$_{20}$ alkyl, benzyl, p-methoxybenzyl, phenyl, triphenylmethyl, tetrahydropyran-2-yl, C$_1$–C$_{20}$-acyl, or T$_1$ and T$_2$, when taken together with the adjacent chains to form a cycle, are the substituent B that represents a —CH$_2$—CH$_2$13 , a 1,2-disubstituted phenyl, a 1,2-disubstituted cyclohexane residue, or a residue of formula

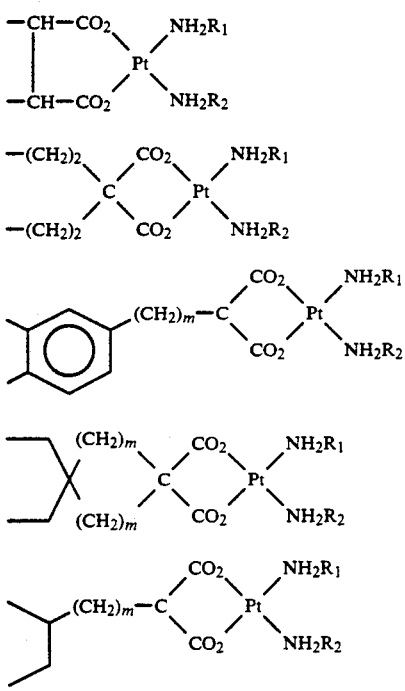

wherein R$_1$ and R$_2$ are as above defined with the proviso that when of n$_1$ or n$_2$ is zero T$_1$ and T$_2$ taken together form a cycle, solvates and isomers thereof. In compounds of formula (I) a C$_1$–C$_{20}$-acyl group represents a residue of a linear or branched aliphatic, cycloaliphatic, aromatic (as benzoic or p-phenylbenzoic), aralkyl and cycloalkylaliphatic (as cyclophenylpropionic or cyclohexylpropionic) acids.

Also the solvatated species as well as the optical antipodes, i.e. the enantiomers, the racemic mixtures of the optical antipodes, the geometric isomers and their mixtures, the diasteroisomers and the mixtures of the diasteroisomers of the compounds of formula (I) are included in the scope of the present invention. Specific examples of preferred compounds of the invention are the following:

cis-(trans-d,l-1,2-diaminocyclohexane)-[2,2-bis(3,6,9-trioxadecane-1-yl)malonate]-platinum(II);
cis(cis-1,2-diaminocyclohexane)-[2,2-bis-(3,6,9-trioxadecane-1-yl)-malonate] platinum(II);
cis[trans(1R,2R)-1,2-diaminocyclohexane]-[2,2-bis(3,6,9-trioxadecane-1-yl)malonate]-platinum (II);
cis(diamino)-[2,2-bis(3,6,9-trioxadecane-1-yl)malonate] platinum(II);
cis(1,2-diaminoethane)-[2,2-bis-(3,6,9-trioxadecane-1-yl)malonate] platinum(II);
cis-(2,3-mesobutanediamine)-[2,2-bis-(3,6,9-trioxadecane-1-yl)malonate] platinum(II);
cis(1,1-diaminomethyl-cylohexane)-[2,2-bis(3,6,9-tricaxadecane-1-yl)-malonate] platinum(II);
(2R, 3R, 11R, 12R)-1,4,7,10,13,16-hexaoxa-cyclooctadecane-2,3-11,12-tetracarbcxylate-bis [cis(tran-d,l-1,2-diamino-cyclohexane)-platinum(II)];
cis(trans-d,l-1,2-diamino-cyclohexane)-1,4,7,10,13,16-hexaoxacyclooctadecane-2,3-dicarboxylate platinum-(II);
(2R,3R,11R,12R)-1,4,7,10,13,16-hexaoxa-cyclooctadecane-(2,3,11,12-tetracarboxylate-bis [cis(trans(1S,2S)-1,2-diaminocyclo-hexane) platinum(II)];
(2R,3R,11R,12R)-1,4,7,10,13,16-hexaoxa-cyclooctadecane-(2, decane-2,3,11,12-tetracarboxylate-bis[cis(-trans(1R,2R)-1,2-diaminocyclo-hexane) platinum-(II)];
(1,7,10,13,19,22-hexaoxacyclotetracosane-4,4,16,16-tetracarboxylate)-bis[cis-(trans-d,l-1,2-diaminocyclohexane) platinum(II)]
and its solvatated species with lithium nitrate;
(1,4,7,10,13,16,19-hexaoxacycloeneicosane-4,4-dicarboxylate)-[cis(trans-d,l-1,2-diamino-cyclohexane) platinum(II)];
(2R,3R,11R,12R)-1,4,7,10,13,16-hexaoxa-cyclooctadecane-2,3,11,12-tetracarboxylate-bis-[cis-(diamino) platinum(II)];
cis-(diamino)-1,4,7,10,13,16-hexaoxa-cyclooctadecane-2,3-dicarboxylate platinum(II).
cis-[(trans-d,l-1,2-diaminocyclohexane)-(1,7,10,13-tetraoxacyclopentadecane-4,4-dicarboxylate)] platinum (II);
cis-[(1,1-diaminomethyl-cyclohexane)-3,3-(1,5,8,11,14,17-hexaoxacyclononadecane)-cyclobutane-1,1-dicarboxylate) ]-platinum(II);
cis-(trans-d,l,1-amino-2-aminomethyl-cyclohexane[(1,4,7,10,-tetraoxacyclododecane-2-yl)methyl]-malonate platinum(II);
cis(trans-d,l-1,2-diaminocyclohexane)[(3,3-[(1,5,8,11,14,17-hexaoxaocyclononadecane)cyclobutane-1, 1-dicarboxylate] platinum(II);
cis(trans-(1R,2R)-diaminocyclohexane-(3,3,-[(1,5,8,11,14,17-hexaoxacyclononadecane)cyclobutane-1, 1-dicarboxylate] platinum (II).

The compounds of the invention are prepared by a process comprising the reaction of a cis-platinum(II) complex of formula (II)

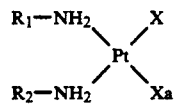

wherein R$_1$ and R$_2$ are as above defined and X and Xa, that can be the same or different are selected in the group of HCO$_3$, NO$_3$, Cl, Br, I or X and Xa taken together are a group of formula:

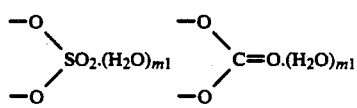

wherein m$_1$ is zero or the integer 1 or 2, with a salt of a carboxylic acid of formula (III)

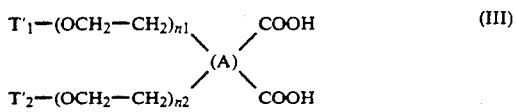

$$T'_1-(OCH_2-CH_2)_{n1} \diagdown \diagup COOH \atop T'_2-(OCH_2-CH_2)_{n2} \diagup (A) \diagdown COOH \qquad (III)$$

wherein $n_1$, $n_2$ and (A) are as above defined and $T'_1$ and $T'_2$ that can be the same or different are selected from the group consisting of: hydrogen, linear or branched $C_1$-$C_{20}$-alkyl, benzyl, p-methoxy-benzyl, triphenylmethyl, tetrahydropyran-2-yl, $C_1$-$c_{20}$ -acyl; or $T'_1$ and $T'_2$ when taken together with the adjacent chains may form a substituent $B_1$ that represents a —$CH_2$—$CH_2$—residue, 1,2-disubstituted phenyl, 1,2-disubstituted cyclohexane or a residue of formula

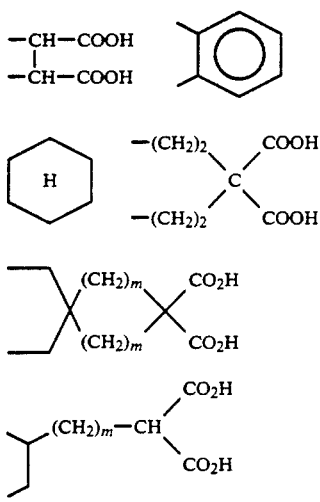

When the compound of formula (III) is a dicarboxylic acid, equimolecular amounts or a slight excess of a compound of formula (II) are preferably used during the complexation reaction, while at least two molar equivalents of a compound of formula (II) are necessary when the compound of formula (III) is a tetracarboxylic acid.

The salts of the acids of formula (III) include cations of mono or bivalent metals selected in the group of lithium, sodium, potassium, rubidium, caesium, magnesium, calcium, strontium, barium or silver.

The salts of acids of formula (III) may be prepared using methods well-known in the art: they can be purified by crystallization or they may be prepared "in situ" by salification of the acid with a solution of a metal hydroxide. Alternatively, the salification of an acid of formula (III) may be also performed in the presence of a compound of formula (II) by addition of stoichiometrical amounts of a metal hydroxide.

The type and nature of the substituents X and Xa of the compounds of formula (II) is dictating the optional selection of the preferred cation of the salts of the acids of formula (III). So, for ex., the use of barium salts of the acids of formula (III) will be particularly preferred when X and Xa together form a sulphate or a carbonate group. On the other hand, the silver salts of the acids of formula (III) will be the most preferred salts when each of X and Xa is a halogen atom.

In both the cases, the complexation reaction gives rise to insoluble salt formation (r.e., $BaSO_4$, $BaCO_3$ or silver halide); the completion of the reaction will be also favoured and the insoluble salts may be easily and advantageously removed by filtration from the reaction mixture.

In an alternative way, in the dark and at room temperature, an aqueous solution of a compound of formula (II), wherein X and Xa are iodine, may be reacted with an aqueous silver nitrate solution for a period of four hours, at least, to give an intermediate complex of formula (II) wherein X and Xa are —$NO_3$, that is not isolated but then reacted with a solution of a salt of a carboxylic acid of formula (III).

Finally, when desired, an aqueous solution of an acid of formula (III) may be also added to a solution of a platinum complex of formula (II) wherein X and $X_a$ taken together are a sulphate group and then the salification of the acid of formula (III) is performed "in situ" by cautious addition of an aqueous solution of an alkaline hydroxide.

Suitable solvents for the reaction of a compound of formula (II) and a salt of an acid of formula (III) are water, lower alcohols such as methanol and ethanol or amides as formamide, dimethylformamide, dimethylacetamide or their mixtures.

The reaction temperature may vary in a range from 0° C. to the boiling point of the solvent used, but the preferred temperature ranges from room temperature and 60° C.; the time reaction may range from some hours to 48 hours.

Cis-platinum complexes of formula (II) are known in the art and may be prepared following known procedures, see for ex. Indian J. Chem., 8, 193, 1970; Inorg. Chim. Acta 91, 223, 1984 and In. Chim. Acta 46, 115, 1980. Many of the carboxylic acids of formula (III) are also described in the current literature see for ex.: (+)-(2R,3R)-1,4,7,10,13,16-hexaoxacyclooctadecane-2,5-dicarboxylic acids, Can. J Chem., 59,1724, 1981 and Synth. Comm., 1771, 1986. Some of them are quite commercially available, as for instance the (+)-(2R,3R,11R,12R)-1,4,7,10,13,16-hexaoxa-cyclo-octadecane-2,3,11,12-tetracarboxylic acid.

In general, the compound of formula (III), when commercially unavailable, may be prepared using known procedures involving alkylation of malonic esters and/or amides as well as etherification of esters and/or N,N-dialkylamides of hydroxy-substituted carboxylic acids to give esters and amides of the acids of the formula(III) that are then hydrolysed using conventional methods. For example, the hydrolysis of said esters may be carried out by treatment with hydroxides of alkali or alkali earth metals in aqueous or hydroalcoholic solutions, while the hydrolysis of amides, for example N,N-dimethylamides, may be conveniently performed using the procedure described in Helv. Chim. Acta, 63, 2096, 1980.

When in compounds of formula (III) the substituent (A) is a tetrasubstituted carbon atom, the carboxylic acids are disubstituted malonic acids that can be prepared by alkylation of malonic esters, in the presence of an alkoxide, with a compound of formulae (IVa) and (IVb):

$$T_i-(OCH_2-CH_2)_{n1}-Y \qquad (IVa)$$

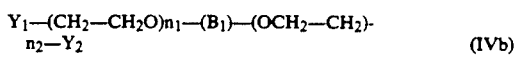
$$Y_1-(CH_2-CH_2O)_{n1}-(B_1)-(OCH_2-CH_2)_{n2}-Y_2 \qquad (IVb)$$

wherein $T_i$ is a linear or branched $C_1$-$C_{20}$-alkyl, phenyl, benzyl, p-methoxybenzyl, triphenylmethyl, tetrahydropyran-2-yl or $C_1$-$C_{20}$-acyl; $n_1$ and $n_2$ are as above defined; Y, $Y_1$ and $Y_2$ are chlorine, bromine, iodine, $CH_3$—$SO_3$—, $C_6H_5$—$SO_3$—, p-$CH_3$—$C_6H_4$—$SO_3$—; $Y_1$ and $Y_2$ when taken together represents a bis functionalised residue of formulae (IV c, d, e):

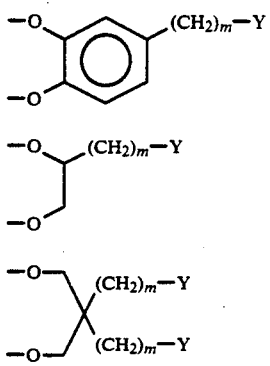

being m and $B_1$ as above defined, to give a compound of formula (Va):

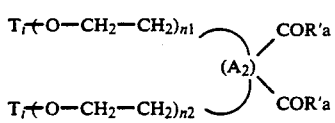

or a compound of formula (Vb):

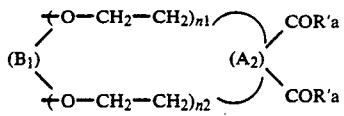

wherein $A_2$, $B_1$, $T_i$, $n_1$ and $n_2$ are as above defined and R'a is a $C_1$-$C_4$-alkoxyl.

When the substituent A of a compound of formula (III) is a 1,1,2,2-tetrasubstituted ethane residue, the substance is a 2,3-dialkoxy-butanedioic acid that may be prepared starting from the N,N,N',N'-tetramethylditartramide by reaction with a compound of formula (IVb) following the procedure described in Synth. Comm. 1771, 1986 so obtaining a compound of formula (Vc):

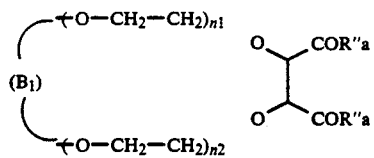

wherein $B_1$ $n_1$ and $n_2$ are as above defined and R''a is a dimethylamine group Preparation of polyoxyethylene compounds of formula (IVa) may be performed starting from commercially available polyoxyethylene glycols of formula (VI): $H(OCH_2$—$CH_2)_{ni}$—OH wherein $n_i$ is an integer from 1 to 20 using known procedures, comprising elongation of the polyoxyethylene chain, mono-acylation or mono-etherification with benzyl or triphenylmethane halides followed by etherification with a suitable alkyl halide, removal of the protecting groups. The appropriate combination of these techniques well-known in the art followed by the removal of the protecting groups allows the preparation of the monosubstituted polyoxyethylene glycols of formula (VII): $T_i$—$(OCH_2$—$CH_2)_{ni}$—OH that are then transformed into the halides or into the sulphonates of formula (IVa) using known methods.

Detailed references concerning these elongation procedures and specific synthesis or on these conventional and well known methods are reported in Synth. Comm., 591, 1984, Acta Chem. Scand. 26, 1471 1962; Synth Comm., 19 1986; Carbohydrate Research 78, 205, 1980. Finally, also compounds of formula(IVc,d) are easily prepared starting from commercially available crown ethers endowed with external hydroxymethyl and/or hydroxyethyl chains, that are then converted in the corresponding halides and/or sulphonates, reacted with malonate esters in the presence of appropriate alkoxide and then hydrolyzed to give the desired malonic acids. Using the same procedure and starting from crown ethers wherein two external hydroxymethyl and/or hydroxyethyl chains are linked to the same carbon atom in the crown compound ( see for their preparation J. Org. Chem., 47, 3478, 1982 and Tetrahed. Lett., 2923, 1983) spiropolyoxyethylene-cycloalkyl-malonic acid of formula (IVe) are prepared, too.

The anti-tumour activity of the compounds of the invention has been investigated "in vitro" and "in vivo" experimental models.

The "in vitro" testing procedure has been based on the "MTT assay on human tumor cell lines" (T. Mosmann, J Immunol. Meth., 65, 55, 1983). According to N.C.I screening program for new anticancer drugs, the evaluation of the anti-tumour activity has been performed against groups of cell lines each representing a major category of human malignancy. Human cell (for ex. cervix epithelioid carcinoma, melanoma, fibrosarcoma and vulvar leiomyosarcoma cultures have been adapted to grow in complete RPMI 1640 medium; the compounds were added to 24 hours cultures and incubated for 72 and 160 hours.

"In vivo" experiments including: a murine leukaemia and murine L1210 leukaemia / cisplatin resistant (i.p. drug administration day 1 after i.p. injection of $10^6$ tumour cells day 0); b) advanced M 5076 ovarian carcinoma in female mice (i.m. injection of $5.10^5$ cell day 0, drug administration q7d×3) are based on classical models that allow a preliminary evaluation of efficacy and toxicity of the novel agent in comparison with a well-stated reference drug. The evaluated parameters are toxic death, median survival time (T/C %) and long term survivals (60 days).

Representative compounds of the invention like:
cis-(trans-d,l-1,2-diaminocyclohexane)-[2,2-bis(3,6,9-tri-oxadecane-1-yl)malonate]-platinum(II) (compound A);
(2R, 3R, 11R, 12R)-1,4-7,10,13,16-hexaoxacyclooctadecane-2,3,11,12-tetracarboxylate-bis-[cis(trans-d,l,-1,2)diamino-cyclohexane)-platinum(II)] (compound B);
cis(trans-d,l-1,2-diamino-cyclohexane)-1,4,7,10,13,16-hexaoxacyclooctadecane-2,3-dicarboxylate platinum-(II) (compound C);
cis[(1,1-diaminomethyl-cyclohexane)-3,3-(1,5,8,11,14,17-hexaoxacyclononadecane)cyclobutane]-1,1-dicarboxylate (compound D);
(2R, 3R, 11R, 12R)-1,4,7,10,13,16-hexaoxacyclooctadecane-2,3-11,12-tetracarboxylate-bis-[cis-1,2-diaminoethane-platinum(II)] (compound E), respectively disclosed in examples 12, 15, 17, 18 and 21 have been investigated in these models in comparison with cis-platin and with cis(1,2-diaminoethane)-(8-hydroxy 3,6-dioxaoctane-1-yl-malonate) platinum (II), chosen as representative example of platinum(II) complexes disclosed in EP 0169645.

As general behaviour, an antitumour activity at least comparable or superior than that of cisplatin has been observed in the tested "in vitro" human cell lines excepting for human melanoma wherein compounds A-E have been found definitely more active than the reference drug. Moreover, compound D is also more active than cisplatin of about a log. order in the cervix epithelioma.

In "in vivo" classical murine L1210, cisplatin administered at 7 and 10 mg/kg has shown a T/C 162% with 1/10 long term survivals.

T/C ranging from 170 to 200% and long term survivals from 1/10 to 3/10 have been determined with the compounds A-E in a dose interval ranging from 20 to 40 mg/kg. No toxic deaths were observed at the effective dosages. For ex. T/C 170%, 2 long term survivor values have been determined with the compound B at 20 mg/kg dose level; toxic side effects appeared at higher doses as 120 mg/kg (2/10 toxic deaths; T/C 200% and 2/10 long term survivors) being $DL_{100}$ over 200 mg/kg.

In the same experiment, the reference compound showed T/C % in a range from 125 to 162 in the dose interval from 15 to 120 mg/kg but at the higher dose level was heavily toxic, too.

Lack of cross resistance with cisplatin was observed when compounds B and D were tested in the L1210 resistant line; T/C % values over 160 have been determined in these experiments (cisplatin T/C 115%) In the M5076 ovarian carcinoma model, compound B showed a tumour growth inhibition potency comparable with that of cisplatin; it is noteworthy that, when tested at equieffective dose levels, animals treated with cisplatin showed a marked body weight decrease while a normal body weight increase was observed after treatment with compound B.

In consideration of their low toxicity and of the good level of anti-tumor activity, the compounds of the present invention are provided with a therapeutical index higher than cis-platinum. Further, the high solubility in water of platinum complexes of the present invention favours the preparation of parenteral and oral pharmaceutical compositions.

The compounds of formula (I) are able to induce regression of the tumor when administered to patients affected with tumors, that may be treated with platinum complexes, at dosages ranging from 1 mg to 1,200 mg per mq of body surface.

The effective dosage of compounds of the invention can be determined by an expert clinician, according to conventional and known methods. Correlation between dosages used for animal of different kinds and human beings (on the basis of mg/m² body surface) is described by Freirich E. J. et al. Quantitative Comparison of Toxicity of Anticancer Agents in Mouse, Rat, Hamster, Dog, Monkey and Man Cancer Chemother. Rep., 50, no. 4, 219-244, May 1966.

The treatment can be appropriately varied, as it is well known to every physician skilled in curing tumors, according to the kind of tumor to be treated and the patient's conditions.

The effective dosage of the compound of the present invention to be administered to patients can be determined with conventional methods. Normally the activity of a platinum(II) complex of the present invention will be evaluated in comparison with other known complexes, such as cis-platinum or carbo-platinum.

The range between therapeutical efficacy and toxicity compared with that of an equivalent known compound will normally determine the appropriate dosage in accordance with conventional dosages of the equivalent compound for the kind of tumour to be treated. Nevertheless, amounts from 1 to 1,200 mg/Kg of the compound will be administered to the patient in a predetermined dosage, with a dosage regimen that will vary in relation with various conditions well known to physicians skilled in the art. Sometimes it will be advantageous to administer the platinum complex of the present invention together with one or more agents increasing anti-tumoral activity and decreasing harmful side-effects of platinum complex. For example platinum complexes of the present invention can be administered together with reduced glutathione, as described in Italian Patent Application no. 48339 A/87 of 1.9 1987.

It is generally admitted that some of platinum complexes having the above formulae could have such a high toxicity or such an unfavourable therapeutical index as to be not suitable for anti-tumor therapy in patients. However, these parameters can be rapidly determined through conventional "screening" pharmacological tests, as for example, with murine leukaemic cells L-1210 implanted in the mouse and said complexes will be of course avoided.

Tumors that can be treated with platinum complexes of this invention are those susceptible to platinum therapy, i.e. tumors that can be treated with cisplatin and carboplatin, as it is known to skilled in the art It is also known that cisplatin and carboplatin have been used up to now for treatment of testicles, ovary, bladder and neck tumors. It is also known that these compounds have a certain, even if limited, activity against lung tumors (non-small cell), osteogenic sarcoma, Hodgkins lymphoma, melanoma and mammary tumors.

Cisplatin showed a certain activity against head and neck "squamous cell carcinoma", against lungs anaplastic tumor (in combination with VP-16, Vinca's alkaloid) against stomach adenocarcinoma, esophagus and prostate carcinoma, osteogenic sarcoma, bones sarcoma, non-Hodgkins lymphoma, mammary adenocarcinoma, brain tumors, endometrium and thyroid tumors. All these tumors should have a good response to treatment with complexes of the present invention. Complexes of the present invention are also active against certain cisplatin resistant tumours shown in studies carried out on animals using said complexes.

Compounds of the invention are preferably administered as sterile aqueous solutions. These solutions are preferably administered by intravenous or intra-arterial route, although other administration forms could be advisable for particular cases. More particularly, compounds of the invention may also be conveniently administered by oral route, because their lypophilicity favours adsorption; efficacy of the treatment will depend for each compound on stability of the complex, on its potency and bio-availability and on absence of topic side-effects.

Pharmaceutical formulations that can be used for parenteral administration include sterile aqueous solutions or powders for an extemporary preparation of the solution, as far as oily preparations for intramuscular or intraperitoneal administration.

Other pharmaceutically useful formulations are syrups or similar liquid preparations, such as solid forms: tablets, capsules or similars.

The following examples illustrate but do not limit the present invention.

The chemical shift (&) values of NMR evaluation reported in the examples are referred to TMS as zero reference.

EXAMPLE 1

A solution of methyl iodide (18,6 g) in 2-butanone (10 ml) is added, dropwise, to a stirred mixture of $K_2CO_3$ (34.5 g) and of 1-hydroxy-3,6,9,12,15,18-hexaoxa-19-phenyl-nonadecane (18.6 g). In a nitrogen atmosphere, the stirred suspension is heated at the reflux temperature for 24 hours, cooled and then filtered. Removal of solvents under vacuum gives 1-phenyl-2,5,8,11,14,17,20-heptaoxaeicosane (17 g) as a clear oil, that is dissolved in methanol (60 ml) and hydrogenated under a 100 bar $H_2$ pressure in the presence of 10% Pd on C (1 g) at 60° C. for 90 min. The cooled suspension is filtered from the catalyst, removal of solvent affords 10 g of 1-hydroxy-3,6,9,12,15,18-hexaoxadecane.

Starting from the corresponding monobenzylether polyoxyethylene glycols and using the same procedure the following monomethylethers are obtained:
1-hydroxy-3,6,9,12,15,18,21,24,27-nonaoxaoctacosane;
1-hydroxy-3,6,9,12,15,18,21,24,27,30,33,36-dodecaoxaheptatricontane.

EXAMPLE 2

Triphenylphosphine (28.82 g) is added, portionwise, to a stirred solution, cooled at 0° C., of 1-hydroxy-3,6,9-trioxadecane (16.4 g and $CBr_4$ (26.48 g) in dry dichloromethane (100 ml). The solution is stirred for additional two hours at room temperature, and then evaporated to dryness under vacuum. The residue is purified by column chromatography ($SiO_2$; hexane/ethyl acetate 4:1) and 17,86 g of 1-bromo-3,6,9-trioxadecane are obtained as a limpid oil - NMR ($CDCl_3$; 3,30, S; 3,60, M).

In similar way, the following halides:
1-bromo-3,6,9,12,15,18-hexaoxanonadecane;
1-bromo-3,6,9,12,15,18,21,24,27-nonaoxaoctacosane;
5 1-bromo-3,6,9,12,15,18,21,24,27,30,33,36-dodecaoxaheptatricontane;
1-bromo-7-phenyl-3,6-dioxaheptane;
1-bromo-3,6-dioxaheptane;
1-bromo-3,6,9-trioxa-10-phenyldecane;
1-bromo-3-oxa-4-phenyl-butane are prepared starting from the corresponding alcohols

EXAMPLE 3

In an inert gas atmosphere, a solution of 1-hydroxy-3,-6,9,12,15,18-hexaoxa-19-phenyl-nonadecane (37.2 g) in tert-butanol (35 ml) is slowly added to a stirred solution of potassium tert-butoxide (12 g) in tert-butanol (150 ml). The mixture is maintained for 1 hour at room temperature, 1-bromo-phenyl-3-oxa-butane (23 g) is added. After heating at the reflux temperature for 4 hours, the solvents are removed in vacuum and the residue is partitioned between water and chloroform. The organic phase is separated, washed with brine and dried on sodium sulphate After solvent removal, the oily residue of 1,24-diphenyl-2,5,8,11,14,17,20,23-octaoxatetraeneicosane (45 g) is hydrogenated (using the procedure of the example 1) to give 3,6,9,12,15,18-hexaoxaeneicosane-1,20-diol (22 g).

EXAMPLE 4

At room temperature, p-toluenesulphonyl chloride (20 g) is added, portionwise, to a stirred solution of 3,6,9-undecane-1,11-diol (19.4 g) in pyridine (200 ml). The mixture is heated at 60° C. for 3 hours, concentrated to small volume and partitioned between 2N $H_2SO_4$ (30 ml) and methylene chloride (100 ml). The organic phase is separated, the aqueous Phase is extracted several times with additional $CH_2 Cl_2$; the combined organic extracts are washed with 5% aqueous $NaHCO_3$, dried on sodium sulphate. Removal of solvent gives 3,6,9-trioxa-undecane -1,11-diol di-p-toluenesulphonate (26 g).

EXAMPLE 5

In an inert gas atmosphere and at room temperature, diethyl malonate (1.73 ml) is added dropwise to a solution of sodium ethoxide (0.77 g) in ethanol (25 ml). After warming at 50° C. for 1 hour, a solution of bromo-3,6,9-trioxadecane (2.6 g) in absolute ethanol (8 ml) is added and warming is prosecuted for an additional hour. A second portion of sodium ethoxide (0.77 g) is added and after additional warming for 1 hour at 50° C., the mixture is treated with an additional portion of a solution f 1-bromo-3,6,9-trioxadecane (2.6 g) in absolute ethanol (8 ml); finally, warming is prosecuted for four hours at 60° C. After removal of the solvent under vacuum, the residue is partitioned between chloroform (40 ml) and brine (10 ml). The organic phase is separated; the aqueous phase is extracted several times with chloroform. The combined organic extracts are dried and the solvent is removed under vacuum. Purification of the oily residue by column chromatography ($SiO_2$; hexane/ethyl acetate 4:1 ethyl acetate) affords 2.21 g of diethyl-2,2-bis(3,6,9-trioxadecane-1-yl)malonate an uncoloured liquid. LiOH monohydrate (0.7 g) is added to aqueous solution of the ester (30 ml). The mixture is heated at 80° C. for three hours, cooled at room temperature and extracted with ethyl acetate (2×4 ml) to remove impurities. The aqueous phase is acidified at pH 1.8 with 2N $H_2SO_4$ and after NaCl addition is extracted with $CHCl_3$. The combined chloroform extracts are dried over $Na_2SO_4$; removal of the solvent yields 1.4 g of 2,2-bis(3,6,9-trioxadecane- 1-yl)malonic acid, as a limpid oil. I.R. (liquid film=3600−2200 $cm^{-1}$; 1227 $cm^{-1}$; 1203 $cm^{-1}$. By reaction of a suitable polyoxyethylenehalide with a dialkylmalonate and by final hydrolysis with lithium hydroxide the following acids:
2,2-bis-(3,6-dioxaheptane-1-yl)-malonic acid;
2,2-bis-(3,6,9,12,15,18-hexaoxanonadecane-1-yl)-malonic acid;
2,2-bis-(3,6,9,12,15,18,21,24,27-nonaoxaoctacosane-1-yl)-malonic acid;
2,2-bis-(3,6,9,12,15,18,21,24,27,30 33,36- dodecaoxaheptatricontane-1-yl)-malonic acid;
2,2-bis(3 6,9-trioxa-10-phenyl-decane-1-yl)-malonic acid are prepared.

EXAMPLE 6

In a nitrogen atmosphere and at room temperature, diethylmalonate (1.52 ml) is added to a suspension of sodium hydride in mineral oil (0.57 g) in dry dimethylformamide (16 ml). After one hour, a solution of 3,6,9-trioxaundecane-1,11-diol di-p-toluenesulphonate (4,38 g) in dry dimethylformamide (7.5 ml) is added and the mixture is heated at 80° C. for 8 hours. After removal of the solvent under vacuum the residue is purified by column chromatography on Al₂O₃ (activity II-III). By elution with toluene, 0.76 g of 4,4,16,16-tetracarbethoxy-1,7,10,13,19,22-hexaoxa-cyclotetracosane are obtained, as a colourless oil. NMR (CDCl₃, TMS) :1,30 t, 12H; 2.20, t, 8H; 3.70, m, 24H;4.12 q, 8H).

An aqueous solution (20 ml) of the tetraester (1.9 g) is warmed in the presence of LiOH.H 0 (0.6 g) at 80° C. for 5 hours. The basic solution is acidified with 6N HCl to pH 2 and lyophilized. The residue is dissolved in a small amount of water and purified on a ionic exchange resin in acid form (Dowex; 50 W x 8). The acid fractions are combined and lyophilized to give 0.83 g of 1,7,10,13,19,22-hexaoxacyclotetracosane-4,4,16,16-tetracarboxylic acid.

NMF (D₂O; TMS) :2 17, t, 8H;3.66, m, 16H.

EXAMPLE 7

In an inert gas atmosphere and at room temperature, diethyl malonate (6.9 ml) is added dropwise to a stirred solution of potassium tert-butoxide (6.8 g) in dry N-methyl pyrrolidone (63 ml). After warming for 1 hour at 60° C. and cooling at room temperature, a solution of pentaethylenene glycol di-p-toluenesulphonate (25 g) n N-methyl pyrrolidone (25 ml) is dropwise added to the mixture over a period of 4 hrs, that is then heated at 80° C. for 18 hrs. After cooling at room temperature, addition of acetic acid (1ml) and removal of the solvent in vacuum, the residue is purified by chromatography on SiO₂ (diethylether/hexane 9:1). The obtained diethyl 2-(14-p-toluenesulphonyloxy-3,6,9,12-tetraoxatetradecane-1-yl)-malonate (4 g) is treated again with potassium tert-butoxide (1.26 g) in dry N-methyl pyrrolidone (50 ml, total volume) using the same procedure above described. A pale yellow oil of 4,4-bis-ethoxycarbonyl-1,7,10,13-tetraoxacyclopentadecane [0.68 g; N.M.R.(CDCl₃): 1.23; 2.30; 3.50-3.71; 4.20] is obtained that is treated with aqueous lithium hydroxide (0.2 g) to give 1,7,10,13-tetraoxacyclopentadecane-4,4-dicarboxylic acid (0.32 g; m.p. 107°-111° C.).

In similar way, 1,7,10,13,16,19-hexaoxacycloenelcosane-4,4-dicarboxylic acid [N.M.R.(CDCl₃): 2.17; 3.64] is prepared starting from 3,6,9,12,15,18-hexaoxaeneicosane -1,20-diol di-p-toluenesulphonate.

EXAMPLE 8

With azeotropic removal of water, a stirred mixture of diethyl malonate (16.7 ml), 3,4-dihydroxybenzaldehyde (14 g), acetic acid (0.3 ml), piperidine (0.5 ml) and toluene (100 ml) is heated at the reflux temperature for 4 hrs. After cooling, dilution with ethyl acetate (200 ml) and washings with water (3×30 ml), the organic phase is dried over sodium sulphate and evaporated to dryness to give ethyl 2-ethoxycarbonyl-3 (3,4-dihydroxyphenyl)-2(Z,E)-propenoate (20 g; m.p. 132°-133° C. from diethylether). Sodium borohydride (15 g) is added portionwise to a solution of 18 g of this latter compound in methanol (200 ml), cooled at 0° C. After 4 hrs at room temperature, a cold aqueous 15% NaH₂PO₄ solution (200 ml) is added to the mixture, the excess of methanol is evaporated in vacuum and the aqueous phase is extracted with ethyl acetate (2×100 ml). The combined organic extracts yields after the usual work-up ethyl 2-ethoxycarbonyl-3-(3,4-dihydroxy-phenyl) -2-propionate [12,3 g; oil, N.M.R. (CDCl₃):1.20; 3.15; 3.51; 6.60-6.92; 7.43; 7.73]

In an inert gas atmosphere, a stirred suspension of this cathecolate 9.6 g and anhydrous potassium carbonate (9.85 g) in dry dimethylformamide is heated at 40° C. for 1 hour, treated with pentaethylene glycol di-p-toluenesulphonate (18 58 g; added in one portion) and warmed at 80° C. for 18 hrs. After removal of the solvent in vacuum, the residue is partitioned between methylene chloride (75 ml) and brine (50 ml). The usual work-up followed by chromatographic purification on basic aluminum oxide (Brockman I methylene chloride/ethanol 99:1, as eluent) affords ethyl 2-ethoxycarbonyl-3-[3,4-(1,4,7,10,13,16-hexaoxahexadecamethylene)-p-henyl ]- propionate as an oil [6.8 g; N.M.R(CDCl₃): 1.20; 3.14; 3.50; 3.67-3.82., 3.87-3.98; 4.15; 6.70-6.82].

The final treatment of an aqueous solution cf this ester with lithium hydroxide (1.44 g) gives the 2-carboxy-3[3,4-(1,4,7,10,13,16-hexaoxahexadecamethylene) -phenyl]-propionic acid as a clear tick oil [4.4 g., N.M.R. (CDCl₃+DMSOd₆): 3.01; 3.47; 3.2-3.60; 3.78-3.81; 3.98-4.07; 6.67].

EXAMPLE 9

In a nitrogen atmosphere, diethyl malonate (14 ml) is slowly added to a stirred solution of potassium tert-butoxide (16 g) in N-methyl pyrrolidone (25 ml) over a period of 1 hour; the mixture is warmed at 50° C. for 1 hour then a solution of triethylene glycol di-p-to-luenesulphonate (25 g) in N-methyl pyrrolidone is added in one portion and warming is continued for additional 18 hrs. After acetic acid addition ( 1 ml) and removal of the solvent in vacuum, the crude residue is diluted with water (30 ml) and extracted with ethyl ether (4×20 ml). The combined organic extracts, after the usual work-up and chromatographic purification on SiO₂ (diethyl ether/hexane 9:1 as eluent) give 1,7,10,16-tetraoxacyclooctadecane-4,4,13,13-tetracarbethoxy (4 g) as a yellow oil. The treatment of an aqueous solution of this ester with lithium hydroxide (1.1 g) gives pure 1,7,10,16-tetraoxocyclooctadecore-4,4,13,13-tetracarboxylic acid ( 2 g) as a pale yellow oil [N.M.R. (CD₃OD): 2.10-2.15; 3.53-3.68; 5.15].

EXAMPLE 10

Reaction in pyridine (13 ml) of 1,4,7,10-tetraoxacyclo-dodecane-2-methanol (5 g) with p-toluenesulphonyl chloride (5 g) produces 1,4,7,10-tetraoxacyclododecane-2-methanol p-toluenesulphonate (8 g; m.p. 49°-51° C. from diethyl ether). Subsequent reaction with diethyl malonate (3.36 ml) and potassium tert-butoxide (3.47 g) in N-methyl pyrrolidone ( 30 ml) yields [(1,4,7,10-tetraoxacyclododecane-2-yl)methyl]-malonate diethyl ester as a viscous oil that is treated with aqueous lithium hydroxide 0.8 g) to obtain pure [(1,4,7,10-tetraoxacyclododecane-2-yl)methyl]-malonic acid N.M.R. (CDCl₃): 2.08-2.19; 3.48-3.82; 9.38].

EXAMPLE 11

Reaction in pyridine (13 ml) of p-toluenesulphonyl chloride (6.2 g) with 3,3-bis-hydroxymethyl-1,5,8,11,14,17-hexaoxacyclononadecane (6.5 g) produces the di-p-toluenesulphonate ( 6.8 g: m.p. 84°-88° C.).

In an inert gas atmosphere, a stirred solution of diethyl malonate (2.45 ml) in isoamyl alcohol (2 ml) is treated with sodium (0.27 g). After about 8 hours, a suspension of the di-tosylate in isoamyl alcohol is added and the mixture is refluxed for 24 hrs. After cooling, sodium p-toluenesulphonate is removed by dilution of the reaction mixture with chloroform and filtration. Solvent removal in vacuum and chromatographic purification of the residue on $SiO_2$ (ethyl acetate/hexane 8:2 as eluent) yield diisoamyl-3,3-(1,5,8,11,14,17-hexaoxacyclononadecane)-cyclobutane-1, 1-dicarboxylate (0.9 g) as a yellow oil, [N.M.R. ($CDCl_3$): 0.9; 1.52; 1.67; 2.43; 3.51; 3.60–3.70; 4.15].

A suspension of the ester in water (5 ml) is heated at 60° C. in the presence of lithium hydroxide (0.2 g) for 24 hrs. The cooled solution is acidified with 2N sulfuric acid, saturated with ammonium sulphate and extracted with tetrahydrofuran (4×20 ml). The combined organic extracts are washed with 40% aqueous ammonium sulphate, dried over $Na_2SO_4$; solvent removal gives:

3,3-(1,5,8,11,14,17-hexaoxacyclononadecane)cyclobutane 1,1-dicarboxylic acid [N.M.R. ($CDCl_3$): 2.48; 3.50–3.65; 6.98].

EXAMPLE 12

An aqueous solution of cis-[trans-d,l-1,2-diaminocyclohexane] platinum(II) sulphate dihydrate (263 mg; 0.6 mM) is added to a stirred solution of 2,2-bis-(3,6,9-trioxadecane-1-yl)-malonate barium salt, prepared by dilution of 5 ml aqueous solution of 0.24 g (0.64 mM) of the acid with 10 ml aqueous solution of barium hydroxide (0.118 g; 0.68 mM). The mixture is kept for 30 min. at room temperature and heated at 60° C. for additional 4 hours. After cooling, the $BaSO_4$ precipitate is removed by centrifugation; the clear filtrate is concentrated to a small volume (10–15 ml), and it is purified by a Sephadex G10 column (empty volume 200 ml) chromatography. After elution with water and eluate lyophilization, 0.2 g of cis-[trans-d,l-1,2-diaminocyclohexane]-[2,2-bis(3,6,9-trioxadecane-1-yl)malonate ] platinum(II) are obtained.

EXAMPLE 13

In accordance with procedure of example 12 by reaction of 2,2-bis(3,6,9-trioxa-decane-1-yl) malonic acid with a suitable diamino-sulphate-platinum(II) complex, the following platinum (II) complexes are obtained:
cis(cis-1,2-diaminocyclohexane)-[2,2-bis-(3,6 9-trioxadecane-1-yl)-malonate] platinum (II);
cis[trans(1R,2R)-1,2-diaminocyclohexane]-[2,2-bis-(3,6,9-trioxadecane-1-yl)-malonate] platinum(II);
cis(diamino)-[2,2-bis-(3,6,9-trioxadecane-1-yl)-malonate] platinum(II);
cis(1,2-diaminoethane)-[2,2-bis-(3,6,9-trioxadecane-1-yl)-malonate] platinum(II);
cis(2,3-mesobutanediamine)-2,2-bis-(3,6,9-trioxadecane-1-yl)-malonate] platinum(II);
cis(1,1-diaminomethyl-cyclohexane)-[2,2-bis-(3,6,9-trioxadecane-1-yl)-malonate] platinum(II).

EXAMPLE 14

In accordance with procedure of example 12, by reaction of cis(trans-d,l-1,2-diaminocyclohexane) sulphate platinum(II) with an appropriate malonic acid the following platinum(II) complexes are prepared:
cis(trans-d,l-1,2-diaminocyclohexane)-[2,2-bis-(3,6,9,12,15,18-hexaoxanonadecane-1-yl)malonate] platinum(II);
cis(trans-d,l-1,2-diaminocyclohexane)-[2,2-bis-(3,6,9,12,15,18,21,24,27,30,33,36-dodecaoxaheptatricontane-1-yl) malonate] platinum(II);
cis(trans-d,l-1,2-diaminocyclohexane)-[2,2-bis-(3,6,9,12,15,18,21,24,27-nonaoxaoctacosane-1-yl)malonate] platinum(II);
cis(trans-d,l-1,2-diaminocyclohexane)-[2,2-bis-(3,6,9 trioxa-10-phenyl-decane-1-yl)-malonate] platinum(II);
cis(trans-d,l-1,2-diaminocyclohexane)-[2,2-bis-(3,6-dioxa-8-hydroxy-octane-1-yl) malonate] platinum (II);
cis(trans-d,l-1,2-diaminocyclohexane)-[2,2-bis-(3,6-dioxaheptane-1-yl)-malonate] platinum(II).

EXAMPLE 15

Over a period of 10 minutes, 0.1N aqueous KOH (22.4 ml 2.24 mM) is slowly added to an aqueous solution (10 ml) of cis(trans-d,l-1,2-diaminocyclohexane) platinum(II) sulphate dihydrate (0.51 g; 1.12 mM and of (2R, 3R. 11R, 12R)-1,4,7,10,13,16-hexaoxacyclooctadecane-2,3,11,12-tetracarboxylic acid (0.25 g; 0.56 mM). The solution is heated at 60° C. for 6 hours and then it is evaporated under vacuum. The residue is extracted several times with methanol/chloroform (5:2); the combined organic extracts are evaporated in vacuum to give 0.55 g of [(2R,3R,11R,12R)-1,4,7,10,13,16-hexaoxa cyclooctadecane-2,3,11,12-tetracarboxylate)]-bis-[cis (trans-d,l-1,2-diaminocyclohexane platinum(II)] hemipotassium sulphate.

Analysis: C, 27.07; H, 4.61; Pt, 32.1; calculated for (PM 1249,3,$C_{28}H_{60}N_4O_{22}S_{0.5}Pt_2K$): C, 26,90; H, 4.80; N, 4.48; Pt, 31.23. IR (RBr)=1820, 1635; 1360, 1100.

EXAMPLE 16

At room temperature and in the dark, a stirred aqueous solution of 0.1 N $AgNO_3$ (20 ml) is added to a suspension of cis(trans-d,l-1,2-diaminocyclohexane-diiodo) platinum(II) (0.52 g) in 5 ml of water. After 4 hours, AgI is filtered off; the filtrate is concentrated in vacuum to 8 ml to give an aqueous solution of cis(trans d,l-1,2-diaminocyclohexane-dinitrate) platinum(II) that is mixed with an aqueous solution of 1,7,10,13-tetraoxa cyclopentadecane-4,4-dicarboxylic acid ( 0.2 g). After addition of a 0.086N LiOH aqueous solution (20.5 ml) over a period of 30 min, the mixture is heated at 60° C. for 7 hrs, cooled at r.t., filtered and evaporated to dryness in vacuum. The excess of lithium nitrate is removed by warm ethanol extraction ( repeated for 4 times) to give a crystalline residue (0.35 g of cis[(trans-d,l-1,2-diaminocyclohexane)-(1 7,10 13-tetraoxacyclopentadecane-4,4-dicarboxylate)] platinum(II).

EXAMPLE 17

At room temperature, a 0.1N KOH aqueous solution (20 ml) is slowly added over a period of 30 min to a stirred solution of cis-(trans-1,2-diaminocyclohexane) -sulphate platinum(II) dihydrate (0.44 g) and of 1,4,7,10,13,16-hexaoxacyclooctadecane-2,3-dicarboxylic acid (0.37 g) in water. The mixture is heated at 60° C. for 8 hrs, evaporated to dryness in vacuum. The residue is repeatedly extracted with methanol/chloroform (5:2); the combined organic extracts are evaporated to dryness to give 0.5 g of cis(trans-d,l-1,2-diaminocyclohexane)-(1,4,7,10,13,17-hexaoxacyclooctadecane-2,3-dicarboxylate) -platinum(II) hemipotassium sulphate.

Analysis: C 29.22; H 4.99; N 3.38. Calculated for (PM 818.2; $C_{20}H_{44}N_2O_{16}PtKS_{0.5}$): C, 29.33; H 5,38; N 3.42.

EXAMPLE 18

In accordance with previous procedure, by reaction of a cis-platinum(II) complex of formula II with:
(+)(2R,3R,11R,12R)-1,4,7,10,13,16-hexaoxacyclo- octadecane-2, 3,11,12-tetracarboxylic acid and 2(RS),3(RS),11(RS),12(RS)-1,4,7,10,13,16-hexaoxacyclo- octadecane-2,3, 11,12-tetracarboxylic acid, and 1,7,10,16,19,22-hexaoxacyclotetracosane-4,4,13,3-tetracarboxylic acid the following compounds are prepared:

(2R,3R,11R,12R)-1,4,7,10,13,16-hexaoxacyclooctadecane-2,3,11,12-tetracarboxylate-bis-[cis(cis-1, 2-diaminocyclohexane-platinum (II)];

(2R,3R,11R,12R)-1,4,7,10,13,16-hexaoxacyclooctadecane-2,3,11,12-tetracarboxylate-bis-[cis (trans-d,l-1,2-diaminocyclohexane-platinum(II)];

(2R,3R,11R,12R)-1,4,7,10,13,16-hexaoxacyclooctadecane-2,3,11,12-tetracarboxylate-bis-[cis (trans(1R,2R)-1,2-diaminocyclohexane-platinum(II)];

(2R,3R,11R,12R,-1,4,7,10 13,16-hexaoxacyclooctadecane-2,3,11,12-tetracarboxylate-bis-[(cis-diamino)-platinum(II)];

(2R,3R,11R,12R)-1,4,7,10,13,16-hexaoxacyclooctadecane-2,3,11,12-tetracarboxylate-bis[cis (aminocyclopentylamino)platinum(II)];

(2R,3R,11R,12R)-1,4,7,10,13,16-hexaoxacyclooctadecane-2,3,11,12-tetracarboxylate-bis-[cis-1, 2-diaminoethane-platinum(II)];

[2(RS),3(RS),12(RS)]-1,4,7,19,13,16-hexaoxacyclooctadecane-2,3,11,12-tetracarboxylate-bis-[cis (trans-d,l-1,2-diaminocyclohexane-platinum(II)];

[2(RS),3(RS),11(RS),12(RS)]-1,4,7,10,13,16-hexaoxacyclooctadecane-2,3,11,12-tetracarboxylate-bis -[cis(-diamino)platinum(II)];

1,4,7,10,16,19-hexaoxacyclotetracosane-4,4,13,13-tetracarboxylate-bis-[cis(trans-d,l-1,2-diaminocyclohexane)platinum (II)];

1,4,7,10,16,19,22-hexaoxacyclotetracosane-4,4,16,16-tetracarboxylate-bis-[cis(trans-1R,2R-1, 2-diaminocyclohexane)platinum(II)];

1,4,7,10,16,19,22-hexaoxacyclotetracosane-4,4,16,16-tetracarboxylate-bis-[cis(diamino)-platinum(II)].

EXAMPLE 19

At room temperature, a 0.09N LiOH aqueous solution (21 ml) is added to a stirred aqueous solution (15 ml) of cis-(1,1-diaminomethyl-cyclohexane)-dinitrate platinum(II), (0.49 g), and 3,3-(1,5,8,11,14,17-hexaoxayclononadecane)-cyclobutane-1,1-dicarboxylic acid (0.25 g). The mixture is warmed at 60° C. for 7 hrs to give, after the usual work-up followed by CHCl3-MeOH extraction, cis[(1,1-diaminomethyl-cyclohexane)-3,3-(1,5,8,11,14,17-hexaoxacyclononadecane)-cyclobutane-1,1-dicarboxylate)9 platinum(II),(0.35g).

EXAMPLE 20

At room temperature, an aqueous stirred solution of cis-(trans-d,l-1-amino-2-aminomethyl-cyclohexane) sulphate platinum(II) dihydrate, 0.8 g, and [(1,4,7,10-tetraoxacycldodecane-2-yl)methyl]-malonic acid, 0.5 g, is treated with aqueous 0.1N KOH (40 ml), slowly added over a period of 30 min. After warming at 60° C. for 8 hours, evaporation to dryness and extraction with methylene chloride/methanol, 0.9 g of cis-(trans-d,l-1-amino-2-aminomethyl-cyclohexane [(1,4,7, 10-tetraoxacylododecane-2-yl)methyl]-malonate platinum (II) are obtained.

In similar way and using 1,7,10,16,-tetraoxacyclooctadecane 4,4,13,13-tetracarboxylic acid, 0.2 g of (1,7,10,16-tetraoxacyclooctadecane-4,4,13,13-tetracarboxylate)-bis-[cis-(trans-d,l-1-amino-2-aminomethyl-cyclohexane) platinum(II)] are prepared.

EXAMPLE 21

At room temperature, a 0.1N KOH aqueous solution (12 ml) is slowly added to a stirred aqueous solution (20 ml) of 2-carboxy-3-[3,4-(1,4,7,10,13,16-hexaoxa-hexadecamethylene)-phenyl]-propionic acid (0.43 g) and of cis(diamino)-sulphate platinum(II) dihydrate (0.4 g) over a period of 20 min. After heating at 60° C. for 7 hours, the mixture is evaporated in vacuum to dryness; the residue is extracted several times with methanol chloroform (5 : 2). The combined organic extracts are evaporated in vacuum to dryness so giving 0.65 g of cis(diamino)-[3,4-(1,4,7,10,13,16-hexaoxa-hexadecamethylene)-phenyl]-ethane -1,1-dicarboxylate platinum-(II).

EXAMPLE 22

Using in one of the previous procedures an appropriate cis-platinum(II) complex of formula II and by reaction with the appropriate di- and/or tetracarboxylic acids the following compounds are prepared:

(1,4,7,10,13,16-hexaoxacyclooctadecane-2,3-dicarboxylate)-[cis-(cis-1,2-diaminocyclohexane)-platinum-(II)];

(1,4,7,10,13,16-hexaoxacyclooctadecane-2,3-dicarboxylate)-[cis-(1,1-diaminomethylcyclohexane)-platinum(II)];

(1,4,7,10,13,16-hexaoxacyclooctadecane-2,3,-dicarboxylate)-[cis-(diamino)-platinum(II)].

(1,7,10,13,16,19-hexaoxacycloeneicosane-4,4-dicarboxylate)-[cis-(trans-d,l-1,2-diaminocyclohexane) platinum(II)];

(1,7,10,13,16,19-hexaoxacycloeneicosane-4,4-dicarboxylate)-[cis(diamino)platinum(II)];

(1,7,10,13,16,19-hexaoxacycloeneicosane-4,4-dicarboxylate)-[cis-(1,1-diaminomethylcyclohexane)-platinum(II)];

cis(trans-(1R,2R)-1,2-diaminocyclohexane)-1,7,10,13-tetraoxacyclopentadecane-4,4-dicarboxylate platinum (II);

cis(1,1-diaminomethyl-cyclohexane)-(1,7,10,13-tetraoxacyclopentadecane-4,4-dicarboxylate) platinum (II);

cis(diamino)-(1,7,10,13-tetraoxacyclopentadecane-4,4-dicarboxylate) platinum (II);

cis(trans-d,l-1-amino-2-aminomethyl-cyclohexane)-(1,7,10,13-tetraoxacyclopentadecane-4,4-dicarboxylate) platinum (II);

cis(trans-d,l-1,2-diaminocyclohexane)[3,3-(1,5,8,11,14,17-hexaoxacyclononadecane)cyclobutane-1,1-dicarboxylate ] platinum(II);

cis(trans-(1R,2R)-diaminocyclohexane)[3,3-(1,5,8,11,14,17-hexaoxacyclonoadecane)cyclobutane-1, 1-dicarboxylate] platinum (II);

cis(trans-1-amino-2-aminomethylcyclohexane)[3,3-(1,5,8,11,14,17-hexaoxacyclonoadecane)cyclobutane-1, 1-dicarboxylate] platinum (II);

cis(diamino)[3,3-(1,5,8,11,14,17-hexaoxacyclononadecanelene) cyclobutane-1,1-dicarboxylate] platinum (II);

cis(1,1-diaminomethylcyclohexane)-[(1,4,7,10-tetraoxacyclodecane-2-yl)methyl]malonate platinum(II);

cis(diamino)-[(1,4,7,10-tetraoxacyclodecane-2-yl)-methyl]malonate platinum(II);

cis(trans-d,l-1,2-diaminocyclohexane)-[(1,4,7,10-tetraoxacyclodecane-2-yl)methyl]malonate platinum-(II);

cis(trans-(1R,2R)-diaminocyclohexane)-[(1,4,7,10-tetraoxacyclodecane-2-yl)methyl]malonate platinum (II);

(1,7,10,16-tetraoxacyclooctadecane-4,4,13,13-tetracarboxylate)-bis-[cis-(trans-1R-amino-2R-aminomethylcyclohexan e) platinum(II)];

(1,7,10,16-tetraoxacyclooctadecane-4,4,13,13-tetracarboxylate)-bis-[cis-(trans-d,l-1,2-diamino-cyclohexane) platinum(II)];

(1,7,10,16-tetraoxacyclooctadecane-4,4,13,13-tetracarboxylate)-bis-[cis-(trans-1R,2R-diamino-cyclohexane) platinum(II)];

(1,7,10,16-tetraoxacyclooctadecane-4,4,13,13-tetracarboxylate)-bis-[cis-(1,1-diaminomethylcyclohexane) platinum(II);

cis(trans-d,l-1,2-diamino-cyclohexane)-[3,4-(1,4,7,10,13,16-hexaoxahexadecamethylene)-phenyl]-ethane1,1-dicarboxylate platinum(II);

cis(1,1-diaminomethylcyclohexane)-[3,4-(1,4,7,10,13,16-hexaoxahexadecamethylene)-phenly]-ethane-1,1-dicarboxylate platinum(II);

cis(trans-d,l-1,1-amino-2-aminomethyl-cyclohexane)-[3,4-(1,4,7,10,13,16-hexaoxadecamethylene)-phenyl]ethane-1,1-dicarboxylate platinum(II).

We claim:

1. Platinum II complexes of formula I

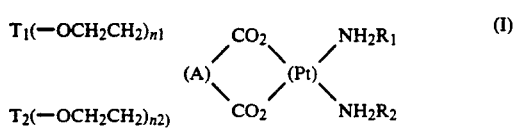

wherein R$^1$ and R$_2$, that can be the same or different, are hydrogen, linear or branched C$_1$–C$_6$-alkyl, C$_3$–C$_6$-cycloalkyl, phenyl, benzyl or, taken together, they represent one of the groups of formula

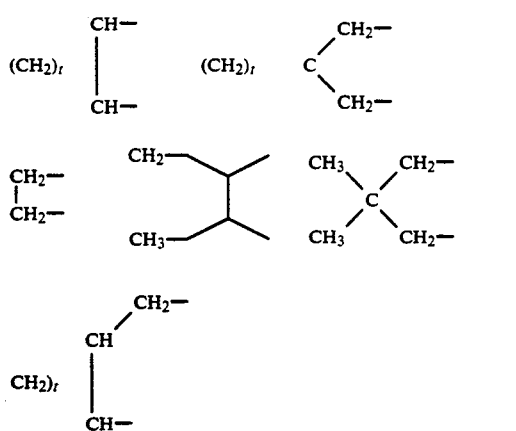

wherein t is an integer from 2 to 5;

(A) is a tetrasubstituted carbon atom or, taken together with the adjacent carboxylate groups, a residue of a dietherified 2,3-dihydroxy-1,4-butanedioic acid, or a residue of mono or disubstituted malonic acids of the following formulae:

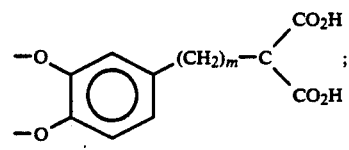

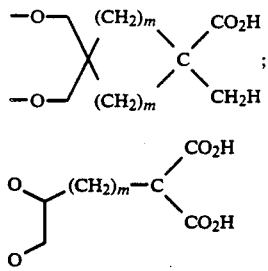

m is the integer 1 or 2;

each of n$_1$ and n$_2$, that may be the same or different, may be independently zero or an integer from 1 to 20 with the proviso that always the overall value of n=(n$_1$+n$_2$) is a number comprised between 2 and 40 so that the overall number of the ethyleneoxy units—(CH$_2$—CH$_2$—O)$_n$—gives a ponderal contribution to the molecular weight of the complex ranging from 88 to 9000 Dalton;

T$_1$ and T$_2$, that can be the same or different, are selected from the group consisting of hydrogen, linear or branched C$_1$–C$_{20}$-alkyl, benzyl, p-methoxybenzyl, phenyl, triphenylmethyl, tetrahydropyran-2-yl, C$_1$–C$_{20}$-acyl, or T$_1$ and T$_2$, when taken together with the adjacent chains to form a cycle, are the substituent B that represents a —Ch$_2$—CH$_2$—, a 1,2-phenylene, a 1,2-cyclohexylene [1,2-disubstituted phenyl, a 1,2-disubstituted cyclohexane residue], or a residue of formula

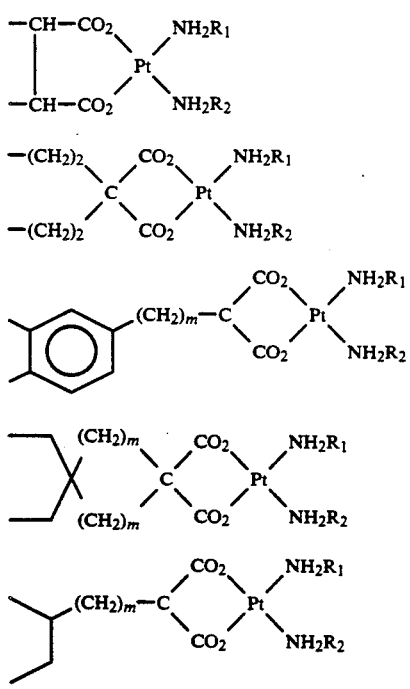

wherein

R$_1$ and R$_2$ are as above defined with the proviso that when one of n$_1$ and n$_2$ is zero T$_1$ and T$_2$ taken together form a cycle;

or a solvate or an isomer thereof.

2. A compound according to claim 1 wherein a C$_1$–C$_{20}$ acyl group represents a residue of formyl, acetyl, benzoic, p-phenylbenzoic, cyclophenylpropionic or cyclohexylpropionic acids.

3. A compound according to claim 1 selected from the group consisting of:
- cis-(trans-d,l-1,2-diaminocyclohexane)-[2,2bis-(3,6,9-trioxadecane-1-yl)malonate]-platinum(II);
- cis(cis-1,2-diaminocyclohexane)-[2,2-bis-(3,6,9-trioxadecane-1-yl)-malonate] platinum(II);
- cis[trans1R,2R)-1,2-diaminocyclohexane]-[2,2-bis-(3,6,9-trioxadecane-1-yl)malonate]-platinum (II);
- cis(diamino)-[2,2-bis(3,6,9-trioxadecane-1-yl)-malonate] platinum(II);
- cis(1,2-diaminoethane)-[2,2-bis-(3,6,9-trioxadecane-1-yl)malonate] platinum(II);
- cis-(2,3-mesobutanediamine)-[2,2-bis-(3,6,9-trioxadecane-1-yl)malonate] platinum(II);
- cis(1,1-diaminomethyl-cyclohexane)-[2,2-bis(3,6,9-tricaxadecane-1-yl)-malonate] platinum(II);
- (2R, 3R, 11R, 12R)-1,4,7,10,13,16-hexaoxa-cyclooctadecane-2,3-11,12-tetracarboxylate-bis[cis(trans d-l-1,2-diamino-cyclohexane)-platinum(II)];
- cis(trans-d,l-1,2-diamino-cyclohexane)-1,4,7,10,13,16-hexaoxacyclooctadecane-2,3-dicarboxylate platinum(II);
- (2R,3R,11R,12R)-1,4,7,10,13,16-hexaoxa-cyclooctadecane-2,3,11,13-tetracarboxylate-bis[cis(trans-(1 S,2S)-1,2-diaminocyclo-hexane) platinum(II)];
- (2R,3R,11R,12R)-1,4,7,10,13,16-hexaoxa-cyclooctadecane-2,3,11,12-tetracarboxylate-bis[cis(trans-(1 R,2R)-1,2-diaminocyclo-hexane) platinum(II)];
- (1,7,10,13,19,22-hexaoxacyclotetracosane-4,4,16,16-tetracarboxylate)-bis[cis-(trans-d,l-1,2diamino-cyclohexane) platinum(II)] and its solvatated species with lithium nitrate;
- (1,4,7,10,13,16,19-hexaoxacycloeneicosane-4,4-dicarboxylate)-[cis(trans-d,l-1,2-diamino-cyclohexane) platinum(II)];
- (2R,3R,11R,12R)-1,4,7,10,13,16-hexaoxa-cyclooctadecane-2,3,11,12-tetracarboxylate-bis-[cis-(diamino) platinum(II)];
- cis-(diamino)-1,4,7,10,13,16-hexaoxa-cyclooctadecane-2,3-dicarboxylate platinum(II).
- cis-[(trans-d,l-1,2-diaminocyclohexane)-(1,7,10,13-tetraoxacyclopentadedane-4,4-dicarboxylate)] platinum (II);
- cis-[(1,1-diaminomethyl-cyclohexane)-3,3-(1,5,8,11,14,17-hexaoxacyclononadecane)-cyclobutane-1,1-dicarboxylate) ]-platinum(II);
- cis-(trans-d,1,1,-amino-2-aminomethyl-cyclohexane-[(1,4,7,10,-tetraoxacyclododecane-2-yl)methyl]-malonate platinum(II);
- cis(trans-d,l-1,2-diamnocyclohexane)(3,3-[(1,5,8,11,14,17-hexaoxacyclononadecane) cyclobutane-1,1-discarboxylate platinum(II):
- cis(trans-(1R,2R)-diaminocyclohexane-(3,3-[(1,5,8,11,14,17-hexaoxacyclonoadecane) cyclobutane-1,1-dicarboxylate]]platinum (II).

4. A pharmaceutical composition suitable for treating tumors, comprising an anti-tumor effective amount of a compound of claim 1 and a pharmaceutically acceptable vehicle.

* * * * *